(12) United States Patent
Day (10) Patent No.: US 11,166,981 B2
(45) Date of Patent: Nov. 9, 2021

(54) METHODS AND COMPOSITIONS FOR TREATING CHLORINE-GAS INDUCED LUNG INJURY

(71) Applicant: National Jewish Health, Denver, CO (US)

(72) Inventor: Brian J. Day, Englewood, CO (US)

(73) Assignee: National Jewish Health, Denver, CO (US)

( * ) Notice: Subject to any disclaimer, the term of this patent is extended or adjusted under 35 U.S.C. 154(b) by 0 days.

(21) Appl. No.: 16/839,480

(22) Filed: Apr. 3, 2020

(65) Prior Publication Data

US 2020/0316108 A1 Oct. 8, 2020

Related U.S. Application Data (60) Provisional application No. 62/828,905, filed on Apr. 3, 2019.

(51) Int. Cl.
*A61K 33/04* (2006.01)
*A61P 11/00* (2006.01)
*A61K 9/00* (2006.01)

(52) U.S. Cl.
CPC ............. *A61K 33/04* (2013.01); *A61P 11/00* (2018.01); *A61K 9/0019* (2013.01); *A61K 9/0048* (2013.01); *A61K 9/0073* (2013.01)

(58) Field of Classification Search
CPC .... A61K 33/04; A61K 9/0037; A61K 9/0048; A61K 9/0019; A61P 11/00
See application file for complete search history.

(56) References Cited

U.S. PATENT DOCUMENTS 10,479,686 B2 * 11/2019 Sherman ............... A61K 31/519

OTHER PUBLICATIONS

White et al., Proc Am Thorac Soc, vol. 7. pp. 257-263, 2010. (Chlorine gas inhalation).*
Sakaguchi et al., Anesthesiology, V 121, No. 6, 2014.(sodium Thiosulfate Attenuates Acute Lung Injury in Mice).*
Cevik et al. "Mass Casualties from Acute Inhalation of Chlorine Gas," Southern Medical Journal, Dec. 2009, vol. 102, No. 12, pp. 1209-1213.
Fanucchi et al. "Post-Exposure Antioxidant Treatment in Rats Decreases Airway Hyperplasia and Hyperreactivity Due to Chlorine Inhalation," American Journal of Respiratory Cell and Molecular Biology, May 2012, vol. 46, No. 5, pp. 599-606.
Ghanei et al. "Long-term pulmonary complications of chemical warfare agent exposure in Iraqi Kurdish civilians," Inhalation Toxicology, 2010, vol. 22, No. 9, pp. 719-724.
Jett et al. "The CounterACT Research Network: Basic Mechanisms and Practical Applications," Proceedings of the American Thoracic Society, Jul. 2010, vol. 7, No. 4, pp. 254-256.
Martin et al. "Chlorine-induced Injury to the Airways in Mice," American Journal of Respiratory and Critical Care Medicine, Sep. 2003, vol. 168, No. 5, pp. 568-574.
Musah et al. "Repair of tracheal epithelium by basal cells after chlorine-induced injury," Respiratory Research, Dec. 2012, vol. 13, No. 1, Article 107, 12 pages.
Oh et al. "Dechlorination with Sodium Thiosulfate Affects the Toxicity of Wastewater Contaminated with Copper, Cadmium, Nickel, or Zinc," Environmental Toxicology, Apr. 2008, vol. 23, No. 2, pp. 211-217.
O'Koren et al. "Loss of Basal Cells Precedes Bronchiolitis Obliterans-Like Pathological Changes in a Murine Model of Chlorine Gas Inhalation," American Journal of Respiratory Cell and Molecular Biology, Nov. 2013, vol. 49, No. 5, pp. 788-797.
Santhanam et al. "Combined electrochemical, sunlight-induced oxidation and biological process for the treatment of chloride containing textile effluent," Chemosphere, Nov. 2017, vol. 186, pp. 1026-1032.
Van Sickle et al. "Acute health effects after exposure to chlorine gas released after a train derailment," The American Journal of Emergency Medicine, Jan. 2009, vol. 27, No. 1, pp. 1-7.
Wenck et al. "Rapid Assessment of Exposure to Chlorine Released from a Train Derailment and Resulting Health Impact," Public Health Reports, Nov.-Dec. 2007, vol. 122, pp. 784-792.
White et al. "Chlorine Gas Inhalation: Human Clinical Evidence of Toxicity and Experience in Animal Models," Proceedings of the American Thoracic Society, Jul. 2010, vol. 7, No. 4, pp. 257-263.
McElroy et al. "Antioxidants as Potential Medical Countermeasures for Chemical Warfare Agents and Toxic Industrial Chemicals," Biochemical Pharmacology, Jan. 2016, vol. 100, pp. 1-11.
Sha et al. Combination of Imipenem and TAK-242, A Toll-Like Receptor 4 Signal Transduction Inhibitor, Improves Survival in a Murine Model of Polymicrobial Sepsis, Shock, 2011, vol. 35, No. 2, pp. 205-209.
Seymour et al. "Murine sepsis phenotypes and differential treatment effects in a randomized trial of prompt antibiotics and fluids," Critical Care, 2019, vol. 23, Article 384, 9 pages.
Zhu et al. "Tomentosin Inhibits Lipopolysaccharide-Induced Acute Lung Injury and Inflammatory Response by Suppression of the NF-κB Pathway in a Mouse Model of Sepsis," Journal of Environmental Pathology, Toxicology and Oncology, 2020, vol. 39, No. 4, pp. 291-298 (Abstract only).

* cited by examiner

*Primary Examiner* — Zohreh A Fay
(74) *Attorney, Agent, or Firm* — Sheridan Ross P.C.

(57) ABSTRACT

The invention provides methods and compositions for treating and/or preventing chlorine-gas induced lung injury with sodium thiosulfate.

13 Claims, 3 Drawing Sheets

METHODS AND COMPOSITIONS FOR TREATING CHLORINE-GAS INDUCED LUNG INJURY

CROSS-REFERENCE TO RELATED APPLICATIONS

This application claims the benefit of priority under 35 U.S.C. § 119(e) to U.S. Provisional Patent Application No. 62/828,905, filed Apr. 3, 2019. The entire disclosure of U.S. Provisional Patent Application No. 62/828,905 is incorporated herein by reference.

BACKGROUND OF THE INVENTION

Figure 1:
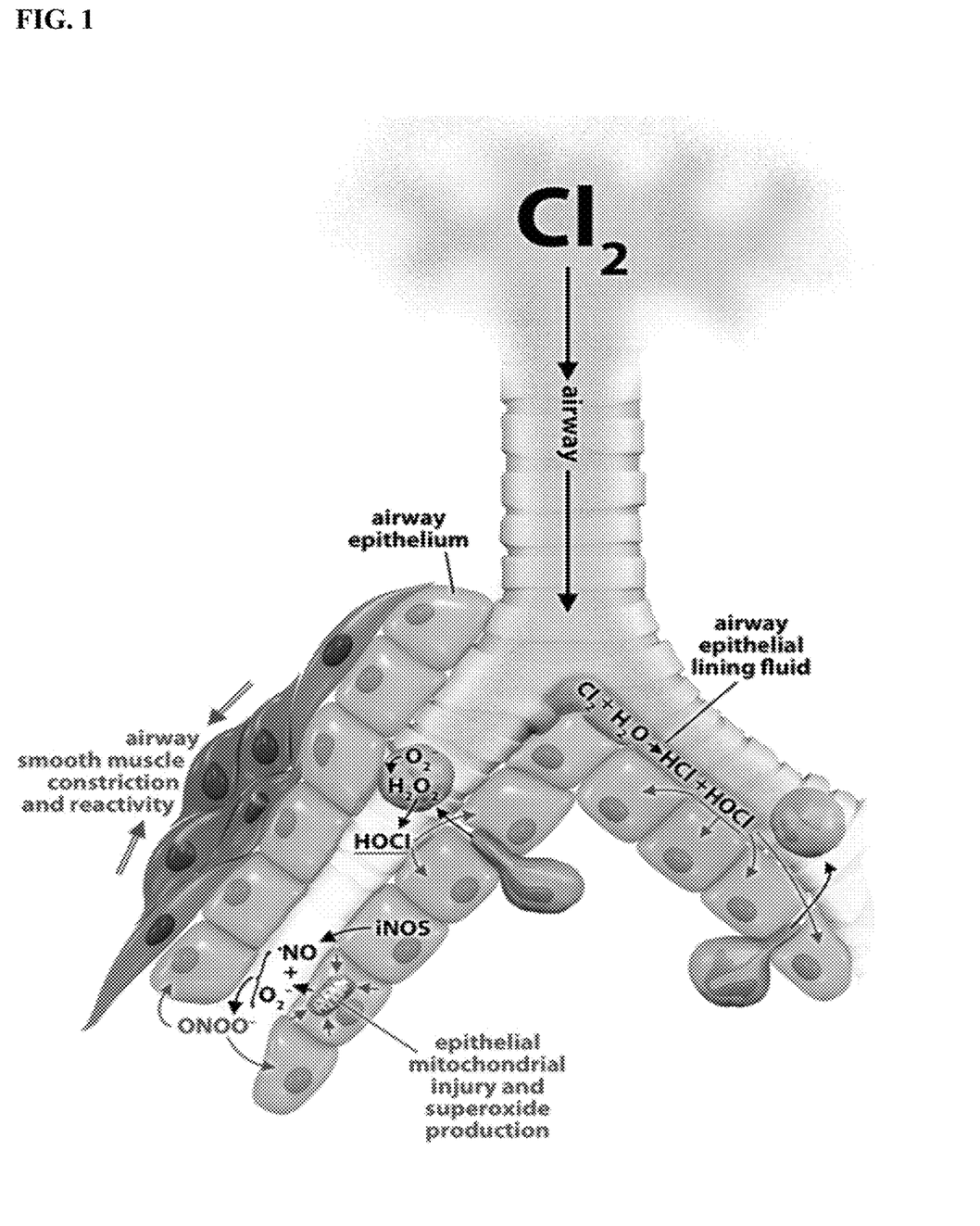
FIG. 1 shows the proposed mechanism for chlorine gas ($Cl_2$)-induced lung injury. Upon contact with airway fluids $Cl_2$ hydrates to form hypochlorous (HOCl) and hydrochloric (HCl) acids. These can damage the airway epithelium leading to inflammation and mitochondrial dysfunction that can further propagate more reactive oxygen and nitrogen species. All these reactive species contribute the lung symptoms associated with $Cl_2$ gas exposures. One mole of sodium thiosulfate ($Na_2S_2O_3$) can rapidly react with 4 moles of sodium hypochlorite (NaOCl) to quickly neutralize further lung injury. (C. W. White, J. G. Martin, Chlorine gas inhalation: human clinical evidence of toxicity and experience in animal models. *Proc Am Thorac Soc* 7, 257-263 (2010)).

The NIH Countermeasures Against Chemical Threats (CounterACT) program goal is to develop post-exposure therapies that prevent or ameliorate morbidity and mortality resulting from exposure to toxic chemicals (D. A. Jett, D. T. Yeung, The CounterACT Research Network: basic mechanisms and practical applications. *Proc Am Thorac Soc* 7, 254-256; C. W. White, J. G. Martin, Chlorine gas inhalation: human clinical evidence of toxicity and experience in animal models. *Proc Am Thorac Soc* 7, 257-263 (2010)). Currently there are no FDA approved effective treatments for exposure to most toxic chemicals which are a concern because they have been deployed as warfare agents or as potential terrorist weapons. Chlorine gas ($Cl_2$) is an example of a chemical agent that has been deployed on military personnel and/or accidental exposures in civilian populations and have produced mass causalities (M. Ghanei et al., Long-term pulmonary complications of chemical warfare agent exposure in Iraqi Kurdish civilians. *Inhal Toxicol* 22, 719-724). Currently there is a lack of effective therapies to mitigate $Cl_2$ gas-induced lung injury. $Cl_2$ gas is a pulmonary irritant that causes acute damage in the upper and lower respiratory tract (C. W. White, J. G. Martin, Chlorine gas inhalation: human clinical evidence of toxicity and experience in animal models. *Proc Am Thorac Soc* 7, 257-263 (2010)). The acute damage can lead to severe pulmonary edema, pneumonia, hyaline membrane formation, and ulcerative tracheobronchitis. Cellular injury is believed to result from the oxidation of functional groups in cellular macromolecules from reactions with tissue fluids that generate hypochlorous (HOCl) and hydrochloric acids (HCl) (FIG. 1).

Chlorine gas is a common toxic inhaled chemical and chemical weapon. Chlorine is a commonly used industrial chemical and in the United States where 13-14 million tons are produced annually. Large quantities of chlorine are transported by rail through heavily populated areas and several railroad accidents have produced spills that have resulted in chlorine gas exposures. Terrorist and military group use of chlorine gas and industrial accidents have produced mass casualties (Y. Cevik, M. Onay, I. Akmaz, S. Sezigen, Mass casualties from acute inhalation of chlorine gas. *South Med J* 102, 1209-1213 (2009); D. Van Sickle et al., Acute health effects after exposure to chlorine gas released after a train derailment. *Am J Emerg Med* 27, 1-7 (2009), M. A.; Wenck et al., Rapid assessment of exposure to chlorine released from a train derailment and resulting health impact. *Public Health Rep* 122, 784-792 (2007)).

Chlorine is a highly produced chemical used in the paper, sanitation, pharmaceutical and chemical industries. Most human exposures of $Cl_2$ gas occur due to exposures to household bleach or $Cl_2$ release from swimming pools. More serious and fatal exposures have occurred during industrial accidents and rail tanker derailments (D. Van Sickle et al., Acute health effects after exposure to chlorine gas released after a train derailment. *Am J Emerg Med* 27, 1-7 (2009), M. A; Wenck et al., Rapid assessment of exposure to chlorine released from a train derailment and resulting health impact. *Public Health Rep* 122, 784-792 (2007)). In the event of $Cl_2$ gas exposure, the most important consideration is the management of the potentially tens of thousands of victims exposed to varying levels of $Cl_2$ gas both during and after the event. An effective countermeasure must be one that is easily administered in the field and effective if given at least 1 hour or more after exposure. $Cl_2$ gas exposures at or above 400 ppm are lethal over 30 minutes and death can occur in minutes at exposure levels of 1,000 ppm and above. The most common clinical finding in accidental $Cl_2$ exposures is wheezing that can persist for an extended period of time after exposure. High levels of $Cl_2$ gas exposure can result in respiratory failure and pulmonary edema due to acute chemical burns of the upper and proximal lower airways (M. V. Fanucchi et al., Post-exposure antioxidant treatment in rats decreases airway hyperplasia and hyperreactivity due to chlorine inhalation. *Am J Respir Cell Mol Biol* 46, 599-606 (2012); J. G. Martin et al., Chlorine-induced injury to the airways in mice. *Am J Respir Crit Care Med* 168, 568-574 (2003); S. Musah, J. Chen, G. W. Hoyle, Repair of tracheal epithelium by basal cells after chlorine-induced injury. *Respir Res* 13, 107 (2012); E. G. O'Koren, B. L. Hogan, M. D. Gunn, Loss of basal cells precedes bronchiolitis obliterans-like pathological changes in a murine model of chlorine gas inhalation. *Am J Respir Cell Mol Biol* 49, 788-797 (2013)).

Chlorine is widely used to purify water and for wastewater treatment (M. Deborde, U. von Gunten, Reactions of chlorine with inorganic and organic compounds during water treatment-Kinetics and mechanisms: a critical review. *Water Res* 42, 13-51 (2008); S. R. Oh, J. K. Kim, M. J. Lee, K. Choi, Dechlorination with sodium thiosulfate affects the toxicity of wastewater contaminated with copper, cadmium, nickel, or zinc. *Environ Toxicol* 23, 211-217 (2008); M. Santhanam, R. Selvaraj, S. Annamalai, M. Sundaram, Combined electrochemical, sunlight-induced oxidation and biological process for the treatment of chloride containing textile effluent. *Chemosphere* 186, 1026-1032 (2017)). Chlorine treatment produces hypochlorous acid and chloramines that are harmful to aquatic organisms. Sodium thiosulfate is commonly used to dechlorinate tap-water for aquariums, ponds and wastewater prior to release into rivers (Y. Du et al., Increase of cytotoxicity during wastewater chlorination: Impact factors and surrogates. *J Hazard Mater* 324, 681-690 (2017)).

There currently are no FDA approved medical countermeasures available to treat $Cl_2$ gas exposures that produce acute lung injury and mortality. Accordingly, there remains a need in the art for new products that effectively treat and/or prevent chlorine gas intoxication.

SUMMARY OF INVENTION

One embodiment of the invention relates to a method of treating chlorine-gas induced lung injury in a subject comprising administering to the subject a therapeutically effective amount of sodium thiosulfate.

In one aspect, the step of administering the sodium thiosulfate is commenced at the onset of acute lung injury symptoms in the subject Another embodiment of the invention relates to a method of preventing chlorine-gas induced lung injury in a subject comprising administering to the subject a therapeutically effective amount of sodium thiosulfate. In one aspect, the sodium thiosulfate is administered prior to exposure of the subject to chlorine gas.

In any of the embodiments of inventions described above, the lung injury is selected from the group consisting of acute respiratory distress syndrome (ARDS), chronic obstructive pulmonary disease (COPD), chemical induced asthma, pulmonary fibrosis, interstitial lung disease, pulmonary edema, pneumonitis and cystic fibrosis lung disease.

In any of the embodiments of inventions described above, the sodium thiosulfate is administered to the subject by an administration route selected from the group consisting of ocular, oral, subcutaneous (SC), intramuscular (IM), and intravenous (IV).

In any of the embodiments of inventions described above, the sodium thiosulfate is administered to the airway of the subject by a delivery method selected from the group consisting of inhalation, nebulization, aerosolization and intratracheal delivery.

In any of the embodiments of inventions described above, the sodium thiosulfate is administered to the eye of the subject by an ocular delivery system. In one aspect, the ocular delivery system is eye drops.

In any of the embodiments of inventions described above, the step of administering comprises administering to the subject an initial dose of the sodium thiosulfate followed by administering an additional dose of the sodium thiosulfate to the subject.

In any of the embodiments of inventions described above, the step of administering the sodium thiosulfate is conducted following the exposure of the subject to chlorine gas.

In any of the embodiments of inventions described above, the step of administering the sodium thiosulfate is conducted immediately after an initial exposure of the subject to chlorine gas.

In any of the embodiments of inventions described above, the step of administering the sodium thiosulfate is conducted within about 1 hour to about 24 hours after an initial exposure of the subject to chlorine gas.

In any of the embodiments of inventions described above, the sodium thiosulfate is administered for at least one week.

Another embodiment of the invention relates to a pharmaceutical composition comprising sodium thiosulfate and a pharmaceutically acceptable carrier or excipient.

DETAILED DESCRIPTION OF THE INVENTION

The invention generally relates to the use of sodium thiosulfate, which is an FDA approved chemical countermeasure against cyanide poisoning, for treating and/or preventing chlorine gas-induced lung injury. Sodium thiosulfate contains a thiol group that not only provides a sulfur group for the cyanide detoxication enzyme rhodanese, but also has antioxidant properties and is a dechlorinating agent (M. Deborde, U. von Gunten, Reactions of chlorine with inorganic and organic compounds during water treatment-Kinetics and mechanisms: a critical review. *Water Res* 42, 13-51 (2008); S. R. Oh, J. K. Kim, M. J. Lee, K. Choi, Dechlorination with sodium thiosulfate affects the toxicity of wastewater contaminated with copper, cadmium, nickel, or zinc. *Environ Toxicol* 23, 211-217 (2008); M. Santhanam, R. Selvaraj, S. Annamalai, M. Sundaram, Combined electrochemical, sunlight-induced oxidation and biological process for the treatment of chloride containing textile effluent. *Chemosphere* 186, 1026-1032 (2017); Y. Du et al., Increase of cytotoxicity during wastewater chlorination: Impact factors and surrogates. *J Hazard Mater* 324, 681-690 (2017)). Data generated by the inventors demonstrates that sodium thiosulfate can protect human lung epithelial cells against hypochlorous acid, the primary oxidant generated during a chlorine gas exposure and glycine chloramine, a secondary oxidant generated during a chlorine gas exposure.

Cellular injury from $Cl_2$ exposure is believed to result from the oxidation of functional groups in cellular macromolecules from reactions with tissue fluids that generate hypochlorous (HOCl) and hydrochloric acids (HCl) (2). These products readily react with thiol and amino groups in proteins and amino acids to produce chloramines that can go on to damage other cellular macromolecules. These oxidants can also produce lipid peroxidation and its aldehyde breakdown products including 4-hydroxynonenal (4-HNE). A number of sensory systems in the lung can be activated by these oxidants and electrophiles including the transient receptor potential (TRP) ion channels in sensory neurons (M. Trevisani et al., 4-Hydroxynonenal, an endogenous aldehyde, causes pain and neurogenic inflammation through activation of the irritant receptor TRPA1. *Proc Natl Acad Sci USA* 104, 13519-13524 (2007)). TRPA1 activation induces respiratory reflexes, inflammation and pain responses (B. F. Bessac et al., TRPA1 is a major oxidant sensor in murine airway sensory neurons. *J Clin Invest* 118, 1899-1910 (2008)). Sodium thiosulfate is a potent dechlorinating agent that rapidly reacts with hypochlorite and secondary reaction products such as chloramines and protects lung epithelial cells from hypochlorite-mediated damage. Secondary exposure to HOCl can result from the innate immune system's response to tissue injury with recruitment of neutrophils and activation of myeloperoxidase (E. G. O'Koren, B. L. Hogan, M. D. Gunn, Loss of basal cells precedes bronchiolitis obliterans-like pathological changes in a murine model of chlorine gas inhalation. *Am J Respir Cell Mol Biol* 49, 788-797 (2013); J. P. Henderson, J. Byun, J. W. Heinecke, Molecular chlorine generated by the myeloperoxidase-hydrogen peroxide-chloride system of phagocytes produces 5-chlorocytosine in bacterial RNA. *J Biol Chem* 274, 33440-33448 (1999); T. K. McGovern et al., Neutrophils mediate airway hyperresponsiveness after chlorine-induced airway injury in the mouse. *Am J Respir Cell Mol Biol* 52, 513-522 (2015)).

Sodium thiosulfate can rapidly react directly with many of chlorine gas decomposition products as well as with reactive species generated by the innate immune system in response to lung injury and inflammation (FIG. 1). This positions sodium thiosulfate as a broad-spectrum medical countermeasure for treating a wide range of chemicals that produce a lung toxidrome. Sodium thiosulfate can rapidly react with HCl and decomposes into sodium chloride, sulfur, sulfur dioxide and water (reaction 1 below).

$$Na_2S_2O_3 + 2HCl \rightarrow 2NaCl + S + SO_2 + H_2O$$

This reaction is known as a version of the "Clock reaction" due to the change in color with defined kinetics (A. F. Holleman, E. Wiberg, *Inorganic Chemistry*. (Academic Press, San Diego, 2001); Y. Hu, G. Xie, D. M. Stanbury, Oxidations at Sulfur Centers by Aqueous Hypochlorous Acid and Hypochlorite: Cl(+) Versus O Atom Transfer. *Inorg Chem* 56, 4047-4056 (2017)). The ability of sodium thiosulfate to rapidly react with most of the reactive products of chlorine gas exposure and low human toxicity makes it an attractive medical countermeasure to test for chlorine gas.

Sodium thiosulfate has a number of other human medical uses besides as an antidote for cyanide poisoning. It has been used to treat calciphylaxis in subjects with end-stage kidney disease (J. S. Cicone, J. B. Petronis, C. D. Embert, D. A. Spector, Successful treatment of calciphylaxis with intravenous sodium thiosulfate. *Am J Kidney Dis* 43, 1104-1108 (2004)). Sodium thiosulfate delayed the progression of coronary artery calcification in hemodialysis subjects (S. Adirekkiat et al., Sodium thiosulfate delays the progression of coronary artery calcification in haemodialysis patients. *Nephrol Dial Transplant* 25, 1923-1929 (2010)). Sodium thiosulfate has antifungal properties and has been employed as a treatment for ringworm (W. K. Jacyk, Four common infectious skin conditions Tinea corporis, *Pityriasis versicolor*, Scabies, Larva migrans. *SA Fam Pract* 46, 13-16 (2004)); has been used to attenuate tissue destruction during extravasations during chemotherapy infusions (J. A. Perez Fidalgo et al., Management of chemotherapy extravasation: ESMO-EONS Clinical Practice Guidelines. *Ann Oncol* 23 Suppl 7, vii167-173 (2012)); has been used to attenuate kidney toxicity (C. E. Pfeifle et al., High-dose cisplatin with sodium thiosulfate protection. *J Clin Oncol* 3, 237-244 (1985)) and hearing loss (D. R. Freyer et al., Effects of sodium thiosulfate versus observation on development of cisplatin-induced hearing loss in children with cancer (ACCL431): a multicentre, randomised, controlled, open-label, phase 3 trial. *Lancet Oncol* 18, 63-74 (2017); E. A. Neuwelt et al., First evidence of otoprotection against carboplatin-induced hearing loss with a two-compartment system in patients with central nervous system malignancy using sodium thiosulfate. *J Pharmacol Exp Ther* 286, 77-84 (1998)) associated with platinum therapy.

Sodium thiosulfate has efficacy in a number of animal injury models. Sodium thiosulfate (0.5-2 g/kg, Intraperitoneal injection (ip) or intravenous (iv)) decreased lung inflammation and injury in LPS and cecal ligation and puncture acute lung injury mouse models even when given post insult (M. Sakaguchi et al., Sodium thiosulfate attenuates acute lung injury in mice. *Anesthesiology* 121, 1248-1257 (2014)). Sodium thiosulfate (1 g/kg, sc) improved mouse survival in a paraquat model of acute lung injury (H. Yamamoto, Protection against paraquat-induced toxicity with sulfite or thiosulfate in mice. *Toxicology* 79, 37-43 (1993)). Sodium thiosulfate was protective in heart ischemia/reperfusion injury rat models (S. Ravindran, S. R. Boovarahan, K. Shanmugam, R. C. Vedarathinam, G. A. Kurian, Sodium Thiosulfate Preconditioning Ameliorates Ischemia/Reperfusion Injury in Rat Hearts Via Reduction of Oxidative Stress and Apoptosis. *Cardiovasc Drugs Ther* 31, 511-524 (2017); S. Ravindran, S. Jahir Hussain, S. R. Boovarahan, G. A. Kurian, Sodium thiosulfate post-conditioning protects rat hearts against ischemia reperfusion injury via reduction of apoptosis and oxidative stress. *Chem Biol Interact* 274, 24-34 (2017)) and cardioprotective in a volume overload heart failure mouse model (U. Sen et al., Cardioprotective role of sodium thiosulfate on chronic heart failure by modulating endogenous H2S generation. *Pharmacology* 82, 201-213 (2008)). Sodium thiosulfate is protective in a number of rat kidney injury models (A. Pasch et al., Sodium thiosulfate prevents vascular calcifications in uremic rats. *Kidney Int* 74, 1444-1453 (2008);) C. A. LaGrange, S. M. Lele, V. M. Pais, Jr., The effect of sodium thiosulfate administration on nephrocalcinosis in a rat model. *J Endourol* 23, 529-533 (2009); P. M. Snijder et al., Sodium thiosulfate attenuates angiotensin II-induced hypertension, proteinuria and renal damage. *Nitric Oxide* 42, 87-98 (2014); R. K. Bijarnia, M. Bachtler, P. G. Chandak, H. van Goor, A. Pasch, Sodium thiosulfate ameliorates oxidative stress and preserves renal function in hyperoxaluric rats. *PLoS One* 10, e0124881 (2015)). Sodium thiosulfate improved survival in a rat model of biliary obstruction that was associated with improved liver mitochondrial function (B. Myslovaty, S. Kyzer, H. Levinsky, C. Chaimoff, Improvement of rat survival and liver mitochondrial function in biliary obstruction after treatment with sodium thiosulfate. *HPB Surg* 8, 249-252 (1995)). Sodium thiosulfate is neuroprotective in a mouse model of global cerebral ischemia/reperfusion (E. Marutani et al., Thiosulfate Mediates Cytoprotective Effects of Hydrogen Sulfide Against Neuronal Ischemia. *J Am Heart Assoc* 4, (2015)) and can attenuate LPS-mediated human glial neuroinflammation, in vitro (M. Lee, E. G. McGeer, P. L. McGeer, Sodium thiosulfate attenuates glial-mediated neuroinflammation in degenerative neurological diseases. *J Neuroinflammation* 13, 32 (2016)). Further, sodium thiosulfate is protective in a guinea pig model of cisplatin-induced ototoxicity even when given post insult (L. L. Muldoon et al., Delayed administration of sodium thiosulfate in animal models reduces platinum ototoxicity without reduction of antitumor activity. *Clin Cancer Res* 6, 309-315 (2000)).

The lung-injury that can be induced by exposure to chlorine gas includes acute respiratory distress syndrome (ARDS), chronic obstructive pulmonary disease (COPD), chemical induced asthma, pulmonary fibrosis, interstitial lung disease, pulmonary edema, pneumonitis or cystic fibrosis lung disease.

Pharmaceutical Compositions

Provided herein are pharmaceutical compositions comprising the sodium thiosulfate provided herein as an active ingredient, alone or in combination with a pharmaceutically acceptable vehicle, carrier, diluent, or excipient, or a mixture thereof.

The sodium thiosulfate provided herein can be administered alone, or in combination with one or more other active ingredients.

The pharmaceutical compositions that comprise the sodium thiosulfate provided herein can be formulated in various dosage forms for ocular, oral, parenteral, and topical administration. The pharmaceutical compositions described herein can also be formulated as modified release dosage forms, including delayed-, extended-, prolonged-, sustained-, pulsa-tile-, controlled-, accelerated- and fast-, targeted-, pro-grammed-release, and gastric retention dosage forms. These dosage forms can be prepared according to conventional methods and techniques known to those skilled in the art (see, Remington: The Science and Practice of Pharmacy, supra; Modified-Release Drug Deliver Technology, Rathbone et al., Eds., Drugs and the Pharmaceutical Science, Marcel Dekker, Inc.: New York, N.Y., 2003; Vol. 126).

In one embodiment, the pharmaceutical composition comprises sodium thiosulfate provided herein and water. In another embodiment, the pharmaceutical composition comprises from about 1 gram to about 100 grams, about 1 gram to about 75 grams, about 1 gram to about 50 grams, about 1 gram to about 25 grams or about 1 gram to about 12.5 grams of sodium thiosulfate provided herein in about 1 mL to about 1000 mL, about 1 mL to about 750 mL, about 1 mL to about 500 mL, about 1 mL to about 250 mL about 1 mL to about 100 mL, about 1 mL to about 50 mL or about 1 mL to about 25 mL of water. In another embodiment, the pharmaceutical composition comprises about 5 grams, about 10 grams, about 12.5 grams, about 15 grams, about 20 grams, about 25 grams, about 30 grams, about 50 grams, about 75 grams or about 100 grams or more of sodium thiosulfate provided herein in about 25 mL, about 50 mL, about 100 mL, about 250 mL, about 500 mL, about 750 mL or about 1000 mL or more of water.

In one embodiment, the pharmaceutical composition comprises sodium thiosulfate provided herein, one or more isotonic agents and one or more pH adjusting agents. In another embodiment, the pharmaceutical composition comprises sodium thiosulfate provided herein, one or more isotonic agents, one or more buffering agents and one or more pH adjusting agents. In a particular embodiment, the pharmaceutical composition comprises sodium thiosulfate provided herein, potassium chloride, boric acid and sodium hydroxide. In a specific embodiment, the pharmaceutical composition comprises sodium thiosulfate provided herein, potassium chloride, boric acid, sodium hydroxide and water (e.g., water for injection).

The pharmaceutical compositions provided herein can be provided in a unit-dosage form or multiple-dosage form. A unit-dosage form, as used herein, refers to a physically discrete unit suitable for administration to a human and animal subject, and packaged individually as is known in the art. Each unit-dose contains a predetermined quantity of the active ingredient(s) sufficient to produce the desired therapeutic effect, in association with the required pharmaceutical carriers or excipients. Examples of a unit-dosage form include an ampoule, syringe, and individually packaged tablet or capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein may be administered at once, or multiple times at intervals of time. It is understood that the precise dosage and duration of treatment can vary with the age, weight, and condition of the patient being treated, and can be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

Oral Administration:

The pharmaceutical compositions provided herein may be provided in solid, semisolid, or liquid dosage forms for oral administration. As used herein, oral administration also includes buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

The pharmaceutical compositions provided herein can be provided as compressed tablets, tablet triturates, chewable lozenges, rapidly dissolving tablets, multiple com-pressed tablets, or enteric-coating tablets, sugar-coated, or film-coated tablets. Enteric-coated tablets are compressed tablets coated with substances that resist the action of stom-ach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cel-lulose acetate phthalate. Film coating imparts the same gen-eral characteristics as sugar coating. Multiple compressed tablets are compressed tablets made by more than one com-pression cycle, including layered tablets, and press-coated or dry-coated tablets.

The pharmaceutical compositions provided herein can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elas-tic capsule (SEC) is a soft, globular shell, such as a gelatin shell, which is plasticized by the addition of glycerin, sorbi-tol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dos-age forms include solutions and suspensions in propylene carbonate, vegetable oils, or triglycerides. Capsules containing such solutions can be prepared as described in U.S. Pat. Nos. 4,328,245; 4,409,239; and 4,410, 545. The capsules may also be coated as known by those of skill in the art in order to modify or sustain dissolution of the active ingredient.

The pharmaceutical compositions provided herein can be provided in liquid and semisolid dosage forms, including emulsions, solutions, suspensions, elixirs, and syr-ups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, dig-lyme, triglyme, tetraglyme, polyethylene glycol-350-dim-ethyl ether, polyethylene glycol-550-dimethyl ether, polyeth-ylene glycol-750-dimethyl ether, wherein 350, 550, and 750 refer to the approximate average molecular weight of the polyethylene glycol. These formulations may further com-prise one or more antioxidants, such as butylated hydroxy-toluene (BHT), butylated hydroxyanisole (BHA), propyl gal-late, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems.

The pharmaceutical compositions provided herein can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Administration:

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein can be administered by topical administration or ocular administration.

The pharmaceutical compositions provided herein can be formulated in any dosage forms that are suitable for parenteral administration, including solutions, suspensions, emulsions, micelles, liposomes, microspheres, nanosystems, and solid forms suitable for solutions or suspensions in liquid prior to injection. The pharmaceutical compositions provided herein can be formulated in any dosage forms that are suitable for topical administration or ocular administration. Such dosage forms can be prepared according to conventional methods known to those skilled in the art of pharmaceutical science (see, Remington: The Science and Practice of Pharmacy, supra) and include eye drops.

The pharmaceutical compositions intended for administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents (e.g., including, but not limited to, potassium chloride, mannitol, sodium chloride, dextran and glucose), buffering agents, antioxidants, local anesthetics, suspending and dispersing agents, wetting or emulsifying agents, complexing agents, sequestering or chelating agents, cryoprotectants, lyoprotectants, thickening agents, pH adjusting agents (e.g., including, but not limited to, an acid, such as boric acid or a base, such as sodium hydroxide), and inert gases.

Suitable aqueous vehicles include, but are not limited to, water, saline, physiological saline or phosphate buff-ered saline (PBS), sodium chloride injection, Ringers injec-tion, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, etha-nol, 1,3-butanediol, liquid polyethylene glycol (e.g., polyeth-ylene glycol 300 and polyethylene glycol 400), propylene glycol, glycerin, N-methyl-2-pyrrolidone, N,N-dimethylac-etamide, and dimethyl sulfoxide.

Suitable antimicrobial agents or preservatives include, but are not limited to, phenols, cresols, mercurials, benzyl alcohol, chlorobutanol, methyl and propyl p-hydroxy-benzoates, thimerosal, benzalkonium chloride (e.g., benze-thonium chloride), methyl- and propyl-parabens, and sorbic acid. Suitable isotonic agents include, but are not limited to, sodium chloride, glycerin, and dextrose.

Suitable buffering agents include, but are not limited to, phosphate and citrate.

Suitable antioxidants are those as described herein, including bisulfite and sodium metabisulfite.

Suitable local anesthetics include, but are not limited to, procaine hydrochloride.

Suitable suspending and dispersing agents are those as described herein, including sodium carboxymethylcelluose, hydroxypropyl methylcellulose, and polyvinylpyrrolidone.

Suitable emulsifying agents include those described herein, including polyoxyethylene sorbitan monolaurate, polyoxyethylene sor-bitan monooleate 80, and triethanolamine oleate.

Suitable sequestering or chelating agents include, but are not limited to EDTA.

Suitable pH adjusting agents include, but are not limited to, sodium hydroxide, hydrochloric acid, citric acid, and lactic acid.

Suitable complexing agents include, but are not limited to, cyclodextrins, including a-cyclodextrin, α-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions provided herein can be formulated for single or multiple dosage administration. The single dosage formulations are packaged in an ampoule, a vial, or a syringe. The multiple dosage parenteral formulations must contain an antimicrobial agent at bacterio-static or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspen-sions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein may be formulated as immediate or modified release dosage forms, including delayed, sustained, pulsed, controlled, targeted, and programmed-release forms.

The pharmaceutical compositions can be formulated as a suspension, solid, semisolid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical com-posi-tions to diffuse through.

Topical Administration:

The pharmaceutical compositions provided herein may be administered topically to the skin, orifices, or mucosa. The topical administration, as used herein, includes (intra) dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions provided herein may also comprise liposomes, micelles, micro spheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Tech-nologies Inc., Tualatin, Oreg.).

The pharmaceutical compositions provided herein can be provided in the forms of ointments, creams, and gels.

Suitable ointment vehicles include oleaginous or hydrocarbon vehicles, including lard, benzoinated lard, olive oil, cot-tonseed oil, and other oils, white petrolatum; emulsifiable or absorption vehicles, such as hydrophilic petrolatum, hydrox-ystearin sulfate, and anhydrous lanolin; water-removable vehicles, such as hydrophilic ointment; water-soluble oint-ment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, Remington: The Science and Practice of Pharmacy, supra). These vehicles are emollient but generally require addition of antioxidants and preservatives.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in Remington: The Science and Prac-tice of Pharmacy, supra.

The pharmaceutical compositions provided herein can be administered ophthalmically in the forms of solutions, drops, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions may be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-hep-tafluoropropane. The pharmaceutical compositions may also be provided as a dry powder for insufflation, alone or in combination with an inert carrier such as lactose or phospho-lipids; and nasal drops. For intranasal use, the powder can comprise a bioadhesive agent, including chitosan or cyclodextrin.

Solutions or suspensions for use in a pressurized container, pump, spray, atomizer, or nebulizer may be formulated to contain ethanol, aqueous ethanol, or a suitable alter-native agent for dispersing, solubilizing, or extending release of the active ingredient provided herein, a propellant as sol-vent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

The pharmaceutical compositions provided herein for topical administration can be formulated to be immediate release or modified release, including delayed-, sustained-, pulsed-, controlled-, targeted, and programmed release.

Modified Release:

The pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dos-age forms include delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient.

Matrix Controlled Release Devices:

The pharmaceutical compositions provided herein in a modified release dosage form can be fabricated using a matrix controlled release device known to those skilled in the art (see, Takada et al in "Encyclopedia of Controlled Drug Delivery," Vol. 2, Mathiowitz Ed., Wiley, 1999).

Osmotic Controlled Release Devices:

The pharmaceutical compositions provided herein in a modified release dosage form can be fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

Targeted Delivery:

The pharmaceutical compositions provided herein can also be formulated to be targeted to a particular tissue, receptor, or other area of the body of the subject to be treated, including liposome-, resealed erythrocyte-, and antibody based delivery systems.

Methods of Use:

In one embodiment, provided herein are methods of treating chlorine-gas induced lung injury in a subject comprising administering to the subject a therapeutically effective amount of sodium thiosulfate. The lung injury is selected from the group consisting of acute respiratory distress syndrome (ARDS), chronic obstructive pulmonary disease (COPD), chemical induced asthma, pulmonary fibrosis, interstitial lung disease, pulmonary edema, pneumonitis and cystic fibrosis lung disease.

In one embodiment, provided herein are methods of preventing chlorine-gas induced lung injury in a subject comprising administering to the subject a therapeutically effective amount of sodium thiosulfate prior to exposure of the subject to chlorine gas.

In one embodiment, provided herein are methods for treating known or suspected chlorine gas exposure, which comprise administering to a subject having or at risk for having chlorine gas exposure, a therapeutically effective amount of sodium thiosulfate provided herein. In one embodiment, the subject is a mammal. In another embodiment, the subject is a human.

Depending on the condition, disorder, or disease, to be treated and the subject's condition, the sodium thiosulfate provided herein may be administered by oral, parenteral (e.g., intramuscular, intraperitoneal, intravenous, intracerebroven-tricular (ICY), intracistemal injection or infusion, subcutane-ous injection, or implant), inhalation, eye drops, nasal, vaginal, rectal, sub lingual, or topical (e.g., transdermal or local) routes of administration, and may be formulated, alone or together, in suitable dosage unit with pharmaceutically acceptable carriers, adjuvants and vehicles appropriate for each route of administration.

The dose may be in the form of one, two, three, four, five, six, or more sub-doses that are administered at appropriate intervals per day. The dose or sub-doses can be administered in the form of dosage units containing from about 10 mg to about 1000 g, from about 10 mg to about 100 g, from about 500 mg to about 50 g, or from about 1 g to about 25 g, active ingredient(s) per dosage unit, and if the condition of the patient requires, the dose can, by way of alternative, be administered as a continuous infusion. In one aspect, the step of administering comprises administering to the subject an initial dose of the sodium thiosulfate followed by administering an additional dose of the sodium thiosulfate to the subject. In one aspect, the step of administering the sodium thiosulfate is conducted following the exposure of the subject to chlorine gas. In still another aspect the step of administering the sodium thiosulfate is conducted immediately after an initial exposure of the subject to chlorine gas.

The step of administering the sodium thiosulfate can be conducted within about 1 hour to about 24 hours after an initial exposure of the subject to chlorine gas. In another aspect, the sodium thiosulfate is administered at least 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, 7 days, 8 days, 9 days, 10 days, 11 days, 12 days, 13 days, 2 weeks after the subject's exposure of the subject chlorine gas.

In one aspect, the step of administering the sodium thiosulfate is commenced at the onset of acute lung injury symptoms in the subject.

In certain embodiments, an appropriate dosage level is about 0.1 to about 100 g per kg patient body weight per day (g/kg per day), about 0.1 to about 50 mg/kg per day, about 0.1 to about 25 mg/kg per day, or about 0.5 to about 10 mg/kg per day, which may be administered in single or multiple doses. A suitable dosage level may be about 0.1 to about 100 mg/kg per day, about 0.5 to about 50 mg/kg per day, or about 0.1 to about 10 mg/kg per day. Within this range the dosage may be about 0.1 to about 1, about 1 to about 10.0, or about 10.0 to about 100 mg/kg per day.

Figure 2:
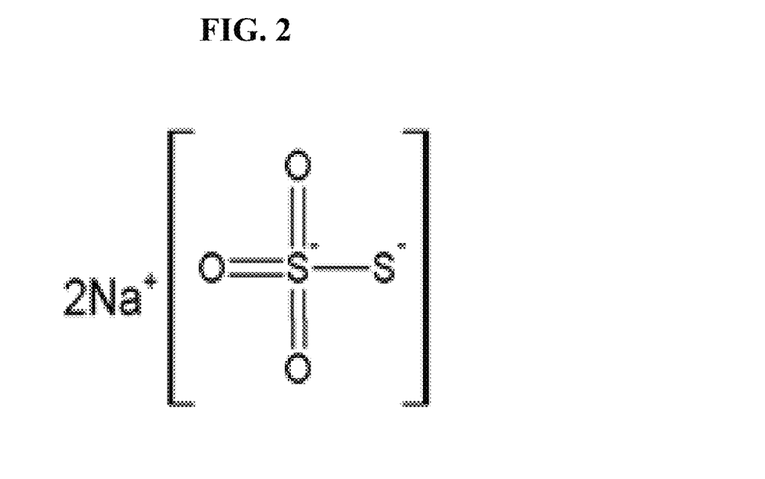
FIG. 2 shows the chemical structure of sodium thiosulfate.

Sodium thiosulfate (FIG. 2) is an FDA approved treatment for acute cyanide poisoning and is used in combination with sodium nitrite and packaged as Nithiodote kit by Hope Pharmaceuticals (Drug Approval Package NDA #203923, Feb. 14, 2012). Each agent is administered separately by slow IV infusion. The toxicity of sodium thiosulfate is low and the reported $LD_{50}$ in animals is 3-4 g/kg. Effective doses in animal models of cyanide toxicity are 150-1000 mg/kg with improvements in survival from 5-70% (V. S. Bebarta et al., Hydroxocobalamin and sodium thiosulfate versus sodium nitrite and sodium thiosulfate in the treatment of acute cyanide toxicity in a swine (*Sus scrofa*) model. *Ann Emerg Med* 55, 345-351 (2010); M. Brenner et al., Oral Glycine and Sodium Thiosulfate for Lethal Cyanide Ingestion. *J Clin Toxicol* 7, (2017)). Current FDA approved dosing of adults for thiosulfate are 200 mg/kg and 100 mg/kg for children. Adverse effects reported for sodium thiosulfate include hypotension, nausea and vomiting. It is also interesting to note that sodium nitrite (the other agent in the Nithiodote kit) has been reported effective in decreasing mortality to chlorine gas exposure by blunting the cardiovascular effects of chlorine in a mouse model (J. Honavar et al., Nitrite therapy improves survival postexposure to chlorine gas. *Am J Physiol Lung Cell Mol Physiol* 307, L888-894 (2014)).

Combination Therapy

The sodium thiosulfate provided herein may also be combined or used in combination with other therapeutic agents useful in the treatment and/or prevention of the diseases and conditions provided herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

As used herein, the term "synergistic" includes a combination of the sodium thiosulfate provided herein and another therapy (e.g., a prophylactic or therapeutic agent) which has been or is currently being used to treat, prevent, or manage a disease or disorder, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention or treatment of a disorder). In addition, a synergistic effect can result in improved efficacy of agents in the prevention or treatment of a disorder. Finally, a synergistic effect of a combination of therapies (e.g., a combination of prophylactic or therapeutic agents) may avoid or reduce adverse or unwanted side effects associated with the use of either therapy alone.

The sodium thiosulfate provided herein can be administered in combination or alternation with another therapeutic agent. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judg-ment of the person administering or supervising the administration of the compositions.

The sodium thiosulfate provided herein can be administered in combination with other classes of compounds, including, but not limited to, transient receptor potential family of ion channel inhibitors (TRP channel inhibitors) such as Ruthenium red, gadolinium $Gd^{3+}$ (homomer), 2-aminoethoxydiphenyl borate (2-APB), lanthanum ion ($La^{3+}$), phorobol myristoyl acetate (PMA), sodium, magnesium, SKF-96365 hydrochloride, caffeic acid, HC-030031, Ethylisopropyl ariloride (EIPA), SAR7334 hydrochloride, SAR7334, 4-(3-Chloro-2-pyridinyl)-N-[4-(1,1-dimethylethyl)phenyl]-1-piperazinecarboxamide (BCTC), Chembridge-5861528, N-[4-[3,5-Bis(trifluoromethyl)-1H-pyrazol-1-yl]phenyl]-3-fluoro-4-pyridinecarboxamide (Pyr6), N-[4-[3,5-Bis(trifluoromethyl)-1H-pyrazol-1-yl]phenyl]-4-methyl-benzenesulfonamide (Pyr10), ML2014 hydrochloride, Mifamurtide; antioxidants, such as cysteine, N-acetyl cysteine, glutathione, ascorbate, and ebselen; vasodilators, such as sodium nitrite; keratolytic agents, such as salicylic acid; endothelin converting enzyme (ECE) inhibitors, such as phosphoramidon; thromboxane receptor antagonists, such as ifetroban; potassium channel openers; thrombin inhibitors, such as hiru-din; growth factor inhibitors, such as modulators of PDGF activity; platelet activating factor (PAF) antagonists; anti-platelet agents, such as GPIIb/IIIa blockers (e.g., abciximab, eptifibatide, and tirofiban), P2Y (AC) antagonists (e.g., clopi-dogrel, ticlopidine and CS-7 47), and aspirin; anticoagulants, such as warfarin; low molecular weight heparins, such as enoxaparin; Factor VIIa Inhibitors and Factor Xa Inhibitors; renin inhibitors; neutral endopeptidase (NEP) inhibitors; vasopeptidase inhibitors (dual NEP-ACE inhibitors), such as omapatrilat and gemopatrilat; HMG CoA reductase inhibi-tors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); squalene synthetase inhibitors; fibrates; bile acid sequestrants, such as questran; niacin; anti-atherosclerotic agents, such as ACAT inhibitors; MTP Inhibitors; calcium channel blockers, such as amlodipine besylate; potassium channel activators; alpha-adrenergic agents; beta-adrenergic agents, such as carvedilol and metoprolol; antiarrhythmic agents; diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; thrombolytic agents, such as tissue plas-minogen activator (tPA), recombinant tPA, streptokinase, urokinase, prourokinase, and anisoylated plasminogen strep-tokinase activator complex (APSAC); anti-diabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thio-zolidinediones (e.g., troglitazone, rosiglitazone, and piogli-tazone), and PPAR-gamma agonists; mineralocorticoid receptor antagonists, such as spironolactone and eplerenone; growth hormone secretagogues; aP2 inhibitors; phosphodi-esterase inhibitors, such as PDE III inhibitors (e.g., cilostazol) and PDE V inhibitors (e.g., sildenafil, tadalafil, and vardenafil); protein tyrosine kinase inhibitors; anti-inflammatories; anti-proliferatives, such as methotrexate, FK506 (tacrolimus), mycophenolate mofetil; chemothera-peutic agents; immunosuppressants; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyrimidine analogues; antibiotics, such as anthracyclines, bleomycins, mitomycin, dactinomycin, and plicamycin; enzymes, such as L-asparaginase; farnesyl-pro-tein transferase inhibitors; hormonal agents, such as gluco-corticoids (e.g., cortisone), estrogens/antiestrogens, androgens/antiandrogens, progestins, and luteinizing hormone-releasing hormone antagonists, and octreotide acetate; microtubule-disruptor agents, such as ecteinascidins; microtubule-stabilizing agents, such as pacitaxel, docetaxel, and epothilones A-F; plant-derived products, such as vinca alkaloids, epipodophyllotoxins, and taxanes; and topoisomerase inhibitors; prenyl-protein transferase inhibitors; and cyclosporins; steroids, such as prednisone and dexamethasone; cytotoxic drugs, such as azathioprine and cyclophosphamide; TNF-alpha inhibitors, such as tenidap; anti-TNF antibodies or soluble TNF receptor, such as etanercept, rapa-mycin, and leflunimide; and cyclooxygenase-2 (COX-2) inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin, and carboplatin.

Provided herein also are kits which, when used by the medical practitioner, can simplify the administration of appropriate amounts of active ingredients to a subject. In certain embodiments, the kit provided herein includes a container and a dosage form of the sodium thiosulfate provided herein.

In certain embodiments, the kit includes a container comprising a dosage form of the sodium thiosulfate provided herein, in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconsti-tuted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injec-tion, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The terms "treat," "treating," and "treatment" are meant to include alleviating or abrogating a disorder, disease, or condition, or one or more of the symptoms associated with the disorder, disease, or condition; or alleviating the cause(s) of the disorder, disease, or condition itself.

The terms "prevent," "preventing," and "prevention" are meant to include a method of delaying and/or precluding the onset of a disorder, disease, or condition, and/or its attendant symptom(s); barring a subject from acquiring a disease; or reducing a subject's risk of acquiring a disorder, disease, or condition.

The term "therapeutically effective amount" is meant to include the amount of a compound, such as sodium thiosulfate, that, when administered, is sufficient to treat or prevent development of, or alleviate to some extent, one or more of the symptoms of the disorder, disease, or condition being treated. The term "therapeutically effective amount" also refers to the amount of a compound, such as sodium thiosulfate, that is sufficient to elicit the biological or medical response of a cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid (e.g., water, such as deionized or sterile water) or solid filler, diluent, excipient, solvent, or encapsulating material. In one embodiment, each component is "pharmaceutically acceptable" in the sense of being com-patible with the other ingredients of a pharmaceutical formu-lation, and suitable for use in contact with cells, tissues, or organs of humans and animals without excessive toxicity, irritation, allergic response, immunogenicity, or other problems or complications, commensurate with a reasonable benefit/risk ratio. See, Remington: The Science and Practice of Pharmacy, 21st Edition, Lippincott Williams & Wilkins Philadelphia, Pa., 2005; Handbook of Pharmaceutical Excipients, 5th Edition, Rowe et al., Eds., The Pharmaceuti-cal Press and the American Pharmaceutical Association: 2005; and Handbook of Pharmaceutical Additives, 3rd Edi-tion, Ash and Ash Eds., Gower Publishing Company: 2007; Pharmaceutical Preformulation and Formulation, Gibson Ed., CRC Press LLC: Boca Raton, Fla., 2004.

The terms "active pharmaceutical ingredient", "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active pharmaceutical ingredient", "active ingredient" and "active substance" may be an optically active isomer of a compound described herein. As used herein, "active pharmaceutical ingredient", "active ingredient", and "active substance" may be the anhydrous, the monohydrate, dihydrate, trihydrate, quatrahydrate, pentahydrate, or other hydrated forms of sodium thiosulfate.

The term "sodium thiosulfate" includes anhydrous, monohydrate, dihydrate, trihydrate, quatrahydrate, pentahydrate, and other hydrated forms of sodium thiosulfate. In one embodiment, the "sodium thiosulfate" referred to herein is sodium thiosulfate pentahydrate ($Na_2S_2O_3 \cdot 5H_2O$). In another embodiment, the sodium thiosulfate is pharmaceutical grade. The term "pharmaceutical grade" as used herein with respect to sodium thiosulfate means that the sodium thiosulfate was manufactured according to Good Manufacturing Practices (GMP) as detailed in the United States Code of Federal Regulations 21 CFR 211 and meets one or more of the purity levels recited herein.

The following experimental results are provided for purposes of illustration and are not intended to limit the scope of the invention.

EXAMPLES

Example 1

Figure 3:
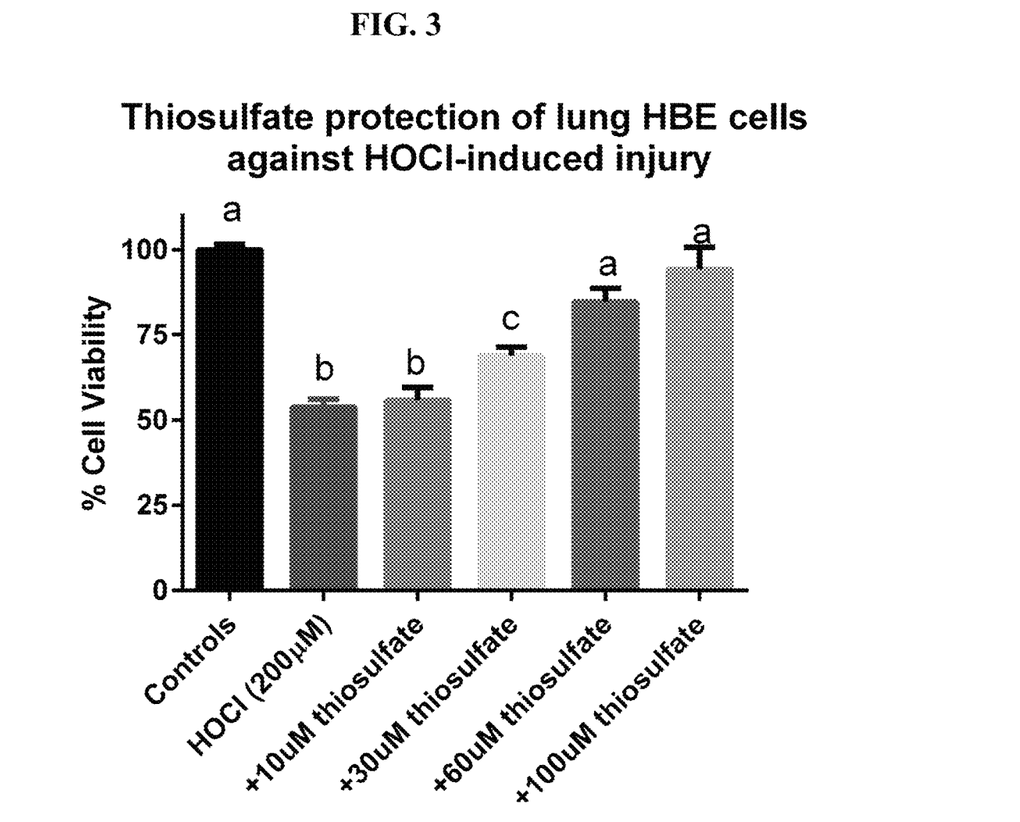
FIG. 3 shows dose-dependent thiosulfate protection of lung Human bronchial epithelial (HBE) cells against HOCl-induced injury. HBE were treated with 200 µM HOCl for 30 minutes and then increasing concentrations of sodium thiosulfate added and cell viability assessed by lactate dehydrogenase (LDH) release 24 hours after oxidant exposure.

This example demonstrates that sodium thiosulfate is effective at ameliorating hypochlorite-induced lung epithelial cell injury. Chlorine gas rapidly decomposes to hypochlorite (HOCl) and hydrochloric acid (HCl) upon contact with aqueous fluids (C. W. White, J. G. Martin, Chlorine gas inhalation: human clinical evidence of toxicity and experience in animal models. *Proc Am Thorac Soc* 7, 257-263 (2010)). Human bronchial epithelial cell line (16HBE) was grown to confluence and treated with 200 µM HOCl in PBS for 30 minutes and then media replaced with DMEM+10% FCS and supplemented with increasing concentrations of sodium thiosulfate. Cell viability was assessed by lactate dehydrogenase (LDH) release 24 hours after HOC treatment. Wells treated with >10 µM of sodium thiosulfate had improved survival against HOC-mediated injury (FIG. 3). These data support the protective effect of sodium thiosulfate against reactive by-products of chlorine gas exposure.

Example 2

This example describes development of a mouse model of chlorine gas-induced acute lung injury and mortality including establishing optimal exposure of $Cl_2$ gas that produces an $LD_{50-70}$ in a mouse model; determines clinically relevant indices of $Cl_2$ gas-induced lung injury in a mouse model and rescue achieved by a therapeutically tolerated dose of sodium thiosulfate. Therapeutic efficacy is defined by clinically relevant endpoints in the mouse chlorine gas model where similar endpoints are measured that have been reported to occur in humans exposed to chlorine gas (D. Van Sickle et al., Acute health effects after exposure to chlorine gas released after a train derailment. *Am J Emerg Med* 27, 1-7 (2009); M. A. Wenck et al., Rapid assessment of exposure to chlorine released from a train derailment and resulting health impact. *Public Health Rep* 122, 784-792 (2007)). These include the measurement of pulse oximetry to determine the lung's ability to oxygen the blood, clinical score assessments of respiratory distress, markers of pulmonary edema, inflammation and oxidative stress. In separate non-lethal chlorine exposures, airway hyperreactivity (AHR) is looked at as it is the most common human complication to chlorine gas exposures (C. W. White, J. G. Martin, Chlorine gas inhalation: human clinical evidence of toxicity and experience in animal models. *Proc Am Thorac Soc* 7, 257-263 (2010)). The inventors have extensive experience measuring these endpoints in both chlorine gas (T. K. McGovern et al., Dimethylthiourea protects against chlorine induced changes in airway function in a murine model of irritant induced asthma. *Respir Res* 11, 138 (2010); T. McGovern, B. J. Day, C. W. White, W. S. Powell, J. G. Martin, AEOL10150: a novel therapeutic for rescue treatment after toxic gas lung injury. *Free Radic Biol Med* 50, 602-608 (2011)) and sulfur mustard gas models (H. C. O'Neill et al., Treatment with the catalytic metalloporphyrin AEOL 10150 reduces inflammation and oxidative stress due to inhalation of the sulfur mustard analog 2-chloroethyl ethyl sulfide. *Free Radic Biol Med* 48, 1188-1196 (2010); H. C. O'Neill et al., Role of reactive oxygen and nitrogen species in olfactory epithelial injury by the sulfur mustard analogue 2-chloroethyl ethyl sulfide. *Am J Respir Cell Mol Biol* 45, 323-331 (2011); C. S. McElroy et al., From the Cover: Catalytic Antioxidant Rescue of Inhaled Sulfur Mustard Toxicity. *Toxicol Sci* 154, 341-353 (2016)).

Optimal exposure of $Cl_2$ gas that produces an $LD_{50-70}$ in a mouse model is established. Although there is literature on mouse models of chlorine exposure, many of these reported studies use different chlorine gas exposure systems, mouse strains, concentrations and duration of exposure. Pilot chlorine dose response studies (400-600 ppm chlorine gas for 30 minutes in C57Bl/6 mice) are run that achieve an $LD_{50-70}$ in the chlorine exposure system within 24 hours. Based on the literature, 12-24 mice per group are needed to achieve significant statistical power to detect a 50-70% effect on mortality (Table 1). Both male and female mice are tested as there have been reports in the literature that female mice are more sensitive than male mice to chlorine gas-induced mortality (J. Honavar et al., Nitrite therapy improves survival postexposure to chlorine gas. *Am J Physiol Lung Cell Mol Physiol* 307, L888-894 (2014)). A non-invasive euthanasia criterion is used to set the mortality endpoint and involves a combination of scoring criteria from the clinical score (7/10 where 10 is death), pulse oximetry (<70%) and body weight loss (>20%) as previously reported (C. S. McElroy et al., From the Cover: Catalytic Antioxidant Rescue of Inhaled Sulfur Mustard Toxicity. *Toxicol Sci* 154, 341-353 (2016)). Chlorine exposure is established that meets the objectives and it is repeated once in both sexes to ensure reproducibility. An additional study is performed at that chlorine concentration, but the duration is changed to 5 minutes to establish a model to test for AHR using 6 mice/group 24 hours post chlorine exposure as previously reported (T. McGovern, B. J. Day, C. W. White, W. S. Powell, J. G. Martin, AEOL10150: a novel therapeutic for rescue treatment after toxic gas lung injury. *Free Radic Biol Med* 50, 602-608 (2011)).

TABLE 1

Exposure study design

| Chlorine exposures (30 min) | Males (n) | Females (n) |
|---|---|---|
| 0 ppm | 12-24 | 12-24 |
| 400 ppm | 12-24 | 12-24 |
| 500 ppm | 12-24 | 12-24 |
| 600 ppm | 12-24 | 12-24 |

Clinically relevant indices of $Cl_2$ gas-induced lung injury in a mouse model. Animals that meet euthanasia requirements are used to determine invasive endpoints to assess potential drug efficacy as done previously in a chlorine model (T. K. McGovern et al., Dimethylthiourea protects against chlorine induced changes in airway function in a murine model of irritant induced asthma. *Respir Res* 11, 138 (2010); T. McGovern, B. J. Day, C. W. White, W. S. Powell, J. G. Martin, AEOL10150: a novel therapeutic for rescue treatment after toxic gas lung injury. *Free Radic Biol Med* 50, 602-608 (2011)) and sulfur mustard gas model (C. S. McElroy et al., From the Cover: Catalytic Antioxidant Rescue of Inhaled Sulfur Mustard Toxicity. *Toxicol Sci* 154, 341-353 (2016)). Mice are euthanized with pentobarbital and lungs fixed either in 10% formalin for histopathology or lavaged with PBS to obtain bronchoalveolar lavage fluid (BALF). A separate set of mice are exposed to a shorter duration of chlorine gas that does not result in mortality and used for assessment of chlorine gas-induced airway hyperreactivity to methacholine challenge (400-600 ppm chlorine for 5 minutes) as described (S. A. Tuck et al., Time course of airway remodelling after an acute chlorine gas exposure in mice. *Respir Res* 9, 61 (2008)). BAL cells are recovered from the BALF by centrifugation. BAL cells are counted and cytospin slides will be prepared for cell differentiation counts. Cell free BALF is assessed for markers of cytotoxicity (lactate dehydrogenase, LDH), edema (protein and IgM levels), and inflammatory cytokines (TNFα, KC and IL-6). Lung tissue is flash frozen in liquid nitrogen and used for measurements of oxidative stress markers (lung tissue 4-HNE, 8-oxo-2dG, nitrotyrosine and glutathione).

Methodology:

Chlorine exposure system: Mice are placed in restraining cones and exposed to chlorine (400-600 ppm) for 30-45 minutes using a nose-only exposure device. $Cl_2$ gas is mixed with room air using a standardized calibrator (VICI Metronics, DYNACALIBRATOR®, model 230-28A). The chlorine delivery system has two main components, a gas generator, which includes a heated permeation chamber and air flow generator. Dynacal permeation tubes designed specifically for operation with the DYNACALIBRATOR®, is used. The permeation chamber and air flow generator control the accuracy of the chlorine generated to within 1-3% of the desired concentration. When the tube containing chlorine is heated the chlorine reaches a constant vapor pressure such that it permeates the tube at a constant rate. The desired concentration is delivered at the flow rate specified by the manufacturer. The device is attached to the exposure chamber and allowed to calibrate for 30 minutes until the optimum temperature of 30° C. is reached.

AHR measurements: Airway hyperreactivity is assessed using a small animal ventilator (flexiVent, Scireq, Montreal, Canada). The flexiVent measures airway responses following inhalation of the bronchoconstrictor methacholine (MCh). This method allows quantification of airway reactivity in various lung compartments, large and small airways and parenchyma. Methacholine is administered using an in-line nebulizer (Aeroneb Lab, standard mist model, Aerogen Ltd, Ireland) and progressively doubling concentrations ranging from 6.25 to 50 mg/ml is administered over 10 seconds synchronously with inspiration. Six measurements are made at each dose of MCh to establish the peak response. The highest value is kept for analysis, subject to a coefficient of determination above 0.85.

Pulse oximetry: A pulse oximeter (Starr Life Sciences, PA) is used to collect heart rates and blood oxygen saturation data from mice prior to chlorine exposure and immediately prior to each thiosulfate injection. Heart rate and pulse oximetry values reported represent the combined mean of 3 running average measurements recorded by the monitoring software.

Clinical scoring: Scoring is run concurrent with the pulse oximetry as a subjective determination of distress. Respiratory quality is scored on a scale of 0-6 and activity on a scale of 0-3 using a previously described method (L. A. Veress et al., Tissue plasminogen activator prevents mortality from sulfur mustard analog-induced airway obstruction. *Am J Respir Cell Mol Biol* 48, 439-447 (2013)). The clinical score represents the summation of both the respiratory quality and activity score where higher distress is indicated by a higher score. The highest score possible in a live animal is 9, whereas a clinical sore of 10 is assigned to a dead animal.

Bronchoalveolar lavage (BAL): Anesthetized mice have a cannula inserted into the trachea for BAL. Lungs are lavaged with 1 mL of PBS twice and the returns pooled. BAL fluid is centrifuged to collect BAL cells for cell counts and differentials. The supernatant is flash frozen in liquid nitrogen for later use to measure markers of lung edema and inflammation (J. D. Chandler et al., Antiinflammatory and Antimicrobial Effects of Thiocyanate in a Cystic Fibrosis Mouse Model. *Am J Respir Cell Mol Biol* 53, 193-205 (2015)).

Lung edema measurement: BALF is analyzed for protein concentrations using the Bicinchonic Acid Protein assay (BCA, Thermo Scientific, IL)) as a measure of lung edema. The levels of BALF IgM is also measured by ELISA (Invitrogen Kit #88-50470-88) as another measure of lung leak. IgM is a large serum protein used to measure lung leak and edema (H. C. O'Neill et al., Treatment with the catalytic metalloporphyrin AEOL 10150 reduces inflammation and oxidative stress due to inhalation of the sulfur mustard analog 2-chloroethyl ethyl sulfide. *Free Radic Biol Med* 48, 1188-1196 (2010)).

Oxidative stress markers: DNA oxidation is measured in lung tissue by the formation of 8-hydroxy-2-deoxyguanosine (8OHdG) as a ratio with non-oxidized 2-deoxyguanosine using HPLC-UV/electrochemical detection (CoulArray Model 5600, ESA, MA) as previously reported (57). Lipid oxidation levels in lung tissues is quantified by analysis of 4-hydroxynonenal (4-HNE) by GC/MS as previously described (H. C. O'Neill et al., Treatment with the catalytic metalloporphyrin AEOL 10150 reduces inflammation and oxidative stress due to inhalation of the sulfur mustard analog 2-chloroethyl ethyl sulfide. *Free Radic Biol Med* 48, 1188-1196 (2010)). Nitrosative stress assessment is made by measuring the formation of nitrotyrosine as a ratio of non-nitrated tyrosine using HPLC-UV/electrochemical detection in lung tissue as previously reported (J. D. Chandler et al., Antiinflammatory and Antimicrobial Effects of Thiocyanate in a Cystic Fibrosis Mouse Model. *Am J Respir Cell Mol Biol* 53, 193-205 (2015)). Glutathione redox status is assessed by measuring glutathione disulfide (GSSG) as a ratio of non-oxidized glutathione (GSH) as previously described (N. S. Gould, E. Min, R. J. Martin, B. J. Day, CFTR is the primary known apical glutathione transporter involved in cigarette smoke-induced adaptive responses in the lung. *Free Radic Biol Med* 52, 1201-1206 (2012)).

Inflammation markers: BAL cell differential counts and BALF levels of a panel of pro-inflammatory cytokines is determined using panel1 V-Plex multi-Spot Assay system (Meso Scale Discovery, MD). This panel measures interferon-gamma (IFN-γ), interleukin-10 (IL-10), IL-12p70, IL-1β, IL-2, IL-4, IL-5, IL-6, KC/GRO, and tumor necrosis factor-alpha (TNF-α). This panel has been previously used with BALF samples (J. D. Chandler et al., Antiinflammatory and Antimicrobial Effects of Thiocyanate in a Cystic Fibrosis Mouse Model. *Am J Respir Cell Mol Biol* 53, 193-205 (2015)).

Lung histopathology: Following chlorine exposure lung tissue is fixed with 4% formalin and used in both immunohistochemistry and immunofluorescence to examine markers of oxidative stress (Nrf2 mRNA expression and protein translocation, 8-oxodg) in lung tissue and airways. Cell apoptosis is assed in airways using TUNEL staining.

Statistical analyses: The survival data is analyzed using Kaplan-Meier plots. Curve comparisons along with survival analysis uses log-rank (Mantel-Cox) approaches to determine hazard ratios (Prism 6 for windows, GraphPad Software, CA). All other analysis uses two-way ANOVA analysis with multiple comparisons (Newman-Keuls post-test) to determine differences between groups at euthanasia. Recently this approach has been used to look at efficacy of drug in sulfur mustard rat model of mortality (C. S. McElroy et al., From the Cover: Catalytic Antioxidant Rescue of Inhaled Sulfur Mustard Toxicity. *Toxicol Sci* 154, 341-353 (2016)). A chlorine exposure is achieved that generates an $LD_{50-70}$ within 24 hours and is used for testing efficacy of sodium thiosulfate.

Example 3

This example demonstrates the dosing route and rescue window for sodium thiosulfate efficacy in a mouse model of chlorine gas-induced acute lung injury and mortality. This is done by determining the sodium thiosulfate pharmacokinetics in mice from three routes of administration, iv, im, sc and optimizing the dose with human dosage used for cyanide intoxication using allometric scaling; determining the sodium thiosulfate route, dose, and dose regimen that mitigates $Cl_2$ gas morbidity and mortality; and determining the effective treatment window of opportunity after $Cl_2$ gas exposure for sodium thiosulfate.

Although sodium thiosulfate is approved for human use as a cyanide antidote, the route of administration is iv infusion and this is not a preferable route of administration for an agent in the counteract program. Two more favorable routes of delivery (im and sc injection) are tested along with some pharmacokinetic studies to assess sodium thiosulfate delivery by sc and im injection. PK analysis determines an approximate equivalent human dose of sodium thiosulfate to test in the chlorine gas exposure mouse model described herein. Standard allometric scaling based on body surface area and area under the curve (AUC) is used for comparisons and adjustments for drug bioavailability from the im and sc routes. The human PK data is available from the Nithiodote kit (Drug Approval Package NDA #203923, Feb. 14, 2012) and from the literature (S. Farese et al., Sodium thiosulfate pharmacokinetics in hemodialysis patients and healthy volunteers. *Clin J Am Soc Nephrol* 6, 1447-1455 (2011)). Thiosulfate is an endogenous compound with basal serum levels of 5.5±1.8 µM in humans (S. Farese et al., Sodium thiosulfate pharmacokinetics in hemodialysis patients and healthy volunteers. *Clin J Am Soc Nephrol* 6, 1447-1455 (2011)). These data allow testing of an equivalent dose of sodium thiosulfate in mice that has already been established as both safe and effective in humans.

Although sodium thiosulfate is approved for human use as a cyanide antidote, there is no literature on doses needed to achieve a therapeutic effect on chlorine-induced lung injury. Thus, the PK analysis is used as a guideline to establish doses, routes and dosing regimens to test for efficacy in the mouse chlorine gas model. The human serum half-life for thiosulfate is reported to be around 3 hours with a high i.v. dose. The im or sc high dose is longer due to an additional absorption phase. The dosing regimen for thiosulfate in humans for acute cyanide poisoning is a bolus iv infusion. In studies performed with nitrite in a murine lethal chlorine exposure model a single bolus im dose was able to improve 24-hour survival when administered as late as 60 minutes post exposure (J. Honavar et al., Nitrite therapy improves survival postexposure to chlorine gas. *Am J Physiol Lung Cell Mol Physiol* 307, L888-894 (2014)). The only two reported studies of thiosulfate use in other mouse lung injury models gave 3 daily (1 g/kg, sc) thiosulfate doses in a 7 day lethal paraquat model (H. Yamamoto, Protection against paraquat-induced toxicity with sulfite or thiosulfate in mice. *Toxicology* 79, 37-43 (1993)) or one bolus dose (0.5 g/kg, iv) 10 minutes after non-lethal cecal ligation and puncture sepsis model (M. Sakaguchi et al., Sodium thiosulfate attenuates acute lung injury in mice. *Anesthesiology* 121, 1248-1257 (2014)). In this example, a single bolus dose is first used based on a human equivalent dose to compare routes (im vs sc) followed by modification of the dosing regimen if necessary.

Sodium thiosulfate has an extended window to start treatment given the delay in first responders to reach victims, thus it is important that treatment is still effective with a 1 hour delay in treatment. Further, efficacy at a 2, 4 and 8 hour delay in starting sodium thiosulfate treatment is also important. Benefits in survival can diminish with delay in starting treatment, but effects on other endpoints such as edema, airway reactivity, clinical scoring can still occur.

Figure 4:
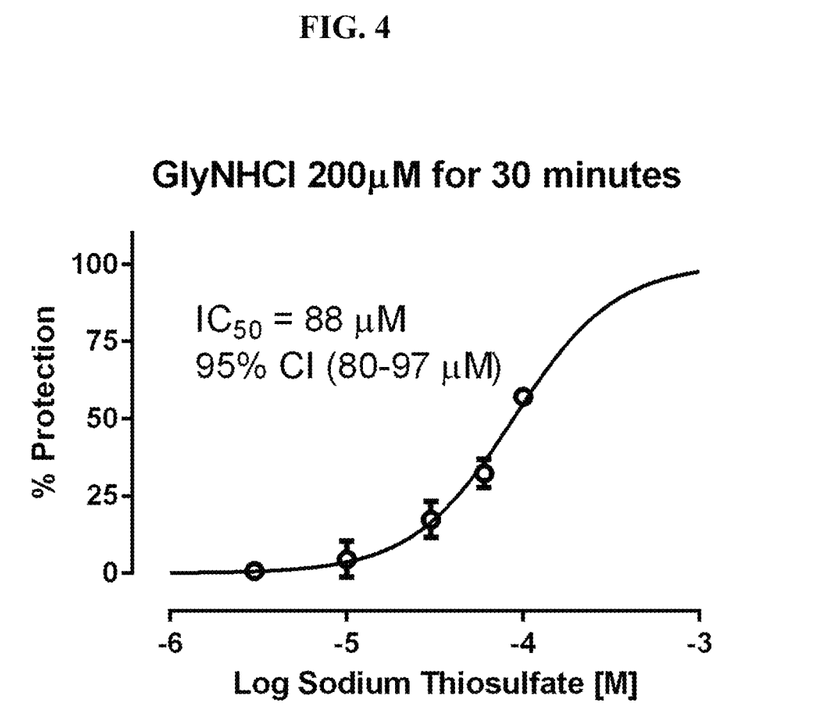
FIG. 4 HBE cells were cultured to confluence in 24 well plates and exposed to 200 mM of glycine chloramine (GLYNHCl) for 30 minutes with or without increasing concentrations of sodium thiosulfate in phosphate buffered saline solution at 37° C. Media was replaced with DMEM containing 5% fetal calf serum and 24 hours later cytotoxicity was assessed using the MTT assay. The inhibitory concentration at 50% ($IC_{50}$) was determined to be 88 mM for sodium thiosulfate with a 95% confidence interval (CI) of 80-97 mM.

A standard PK assessment of thiosulfate in mice is performed using the allometric scaled dose from man to mouse (factor of 12). Human dose is 200 mg/kg, thus a mouse starting dose of 1.0 g/kg is used (actual scale dose could be 2.4 g/kg) which is below the reported 4 g/kg LDso dose for thiosulfate for iv route. The 1 g/kg dose has been safely used in other mouse models of lung injury or animals models of cyanide poisoning. Groups of 4 mice (both sexes) are used for each time point with each route of delivery (iv, im and sc) with the time points of 0.5, 1, 2, 4, 6, 8 and 24 hour time points being looked at to obtain serum and lung tissue thiosulfate levels by HPLC with fluorescence detection as previously reported for human serum (M. Shea, S. Howell, High-performance liquid chromatographic measurement of exogenous thiosulfate in urine and plasma. *Anal Biochem* 140, 589-594 (1984); M. Shea, J. A. Koziol, S. B. Howell, Kinetics of sodium thiosulfate, a cisplatin neutralizer. *Clin Pharmacol Ther* 35, 419-425 (1984)). A modified method in the laboratory has been established and the inventors have found it to be sensitive (>1 µM thiosulfate in plasma) for detecting thiosulfate in mouse plasma (FIG. 4). Pharmacokinetic modeling is done on collected data to determine serum elimination half-life ($T_{1/2}$), peak concentration (Cmax), time to peak concentration (Tmax), and area under the curve (AUC) using PKAnalyst software (MicroMath, UT). Bioavailability is determined by comparing AUCs from sc and im routes to that from iv route. These data are compared to the reported human PK for thiosulfate. Similar PK analysis have been performed by the inventors for drug efficacy studies with nerve agents (L. P. Liang et al., Neuroprotective Effects of AEOL10150 in a Rat Organophosphate Model. *Toxicol Sci*, (2017)).

A 2×2 study design (Table 2) is used to compare im and sc routes of thiosulfate delivery on efficacy in the mouse chlorine exposure model. Thiosulfate is given at 1 g/kg 60 minutes post chlorine exposure and mortality is assessed 24 hours post exposure. Other endpoints are collected at euthanasia. Both males and females are tested separately using chlorine exposure conditions established above. An additional study is also run in both sexes to assess 7 day mortality in surviving mice to see if thiosulfate has any effect on the delayed toxicity reported in this model. The best efficacy route is moved forward to optimize dose and/or dose regimen. Optimized parameters are replicated once in both sexes.

TABLE 2

Thiosulfate (1 g/kg) Efficacy comparing im to sc routes

| | im delivery | | sc delivery | |
|---|---|---|---|---|
| | PBS | Thiosulfate | PBS | Thiosulfate |
| Filtered air | 12-24 mice | 12-24 mice | 12-24 mice | 12-24 mice |
| Chlorine gas | 12-24 mice | 12-24 mice | 12-24 mice | 12-24 mice |

The study design in Table 2 is used to extend the delay in treatment with thiosulfate from 1 hour post chlorine exposure to 2 hours post exposure. Further, another study at 4 hours post exposure and up to 8 hours post exposure is run.

The mouse studies are designed based on previous experience using similar chlorine gas exposures and outcome measurements to determine study power requirements (T. K.

McGovern et al., Neutrophils mediate airway hyperresponsiveness after chlorine-induced airway injury in the mouse. *Am J Respir Cell Mol Biol* 52, 513-522 (2015); T. K. McGovern et al., Dimethylthiourea protects against chlorine induced changes in airway function in a murine model of irritant induced asthma. *Respir Res* 11, 138 (2010); T. McGovern, B. J. Day, C. W. White, W. S. Powell, J. G. Martin, AEOL10150: a novel therapeutic for rescue treatment after toxic gas lung injury. *Free Radic Biol Med* 50, 602-608 (2011); T. McGovern et al., CysLT1 Receptor Is Protective against Oxidative Stress in a Model of Irritant-Induced Asthma. *JImmunol* 197, 266-277 (2016)). A 2×2 study design is used to control for each group variable and to look for variable interactions. Both sexes are studied due to recent published literature that suggests a strong sex effect in female mice that may help inform dosing strategies. C57bl/6 strain is ordered from only one vender to ensure consist genetic background and reproducibility. All studies are reproduced at least twice to ensure reproducibility.

Example 4

This example demonstrates administration of sodium thiosulfate to subjects exposed to chlorine gas and who develop respiratory distress. Such subject can include, workers in a chemical plant where an accidental chlorine leak occurs; soldiers on a battlefield were chlorine gas is deployed as a chemical weapon; civilians exposed to chlorine gas as a result of terrorism; subjects exposed to chlorine gas due to the mixing of chemicals that result in chlorine gas generation such as used to chlorinate water or mixing of cleaning agents.

For the above cases, sodium thiosulfate is given prophylaxis to first responders or soldiers entering an area of chlorine gas generation to prevent chlorine gas mediated respiratory distress. Sodium thiosulfate can also be given to individuals post exposure of chlorine gas to rescue or diminish lung injury from the chlorine gas exposure.

Example 5

This example demonstrates administration of sodium thiosulfate to subjects with chronic lung diseases that result from chronic inflammation and injury due to innate immune system generation of hypochlorous acid. A situation where a subject has an exacerbation of chronic lung disease such as acute respiratory distress syndrome (ARDS), bronchopulmonary dysplasia (BPD), chronic obstructive pulmonary disease (COPD), asthma, pulmonary fibrosis, interstitial lung disease, pulmonary edema, pneumonitis or cystic fibrosis lung disease. Sodium thiosulfate is given during the exacerbation to improve lung function or prophylaxis to diminish the loss of lung function.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following exemplary claims.

REFERENCES

1. D. A. Jett, D. T. Yeung, The CounterACT Research Network: basic mechanisms and practical applications. *Proc Am Thorac Soc* 7, 254-256.
2. C. W. White, J. G. Martin, Chlorine gas inhalation: human clinical evidence of toxicity and experience in animal models. *Proc Am Thorac Soc* 7, 257-263 (2010).
3. M. Shea, S. Howell, High-performance liquid chromatographic measurement of exogenous thiosulfate in urine and plasma. *Anal Biochem* 140, 589-594 (1984).
4. M. Ghanei et al., Long-term pulmonary complications of chemical warfare agent exposure in Iraqi Kurdish civilians. *Inhal Toxicol* 22, 719-724.
5. M. Deborde, U. von Gunten, Reactions of chlorine with inorganic and organic compounds during water treatment-Kinetics and mechanisms: a critical review. *Water Res* 42, 13-51 (2008).
6. S. R. Oh, J. K. Kim, M. J. Lee, K. Choi, Dechlorination with sodium thiosulfate affects the toxicity of wastewater contaminated with copper, cadmium, nickel, or zinc. *Environ Toxicol* 23, 211-217 (2008).
7. M. Santhanam, R. Selvaraj, S. Annamalai, M. Sundaram, Combined electrochemical, sunlight-induced oxidation and biological process for the treatment of chloride containing textile effluent. *Chemosphere* 186, 1026-1032 (2017).
8. Y. Du et al., Increase of cytotoxicity during wastewater chlorination: Impact factors and surrogates. *J Hazard Mater* 324, 681-690 (2017).
9. Y. Cevik, M. Onay, I. Akmaz, S. Sezigen, Mass casualties from acute inhalation of chlorine gas. *South Med J* 102, 1209-1213 (2009).
10. D. Van Sickle et al., Acute health effects after exposure to chlorine gas released after a train derailment. *Am J Emerg Med* 27, 1-7 (2009).
11. M. A. Wenck et al., Rapid assessment of exposure to chlorine released from a train derailment and resulting health impact. *Public Health Rep* 122, 784-792 (2007).
12. M. V. Fanucchi et al., Post-exposure antioxidant treatment in rats decreases airway hyperplasia and hyperreactivity due to chlorine inhalation. *Am J Respir Cell Mol Biol* 46, 599-606 (2012).
13. J. G. Martin et al., Chlorine-induced injury to the airways in mice. *Am J Respir Crit Care Med* 168, 568-574 (2003).
14. S. Musah, J. Chen, G. W. Hoyle, Repair of tracheal epithelium by basal cells after chlorine-induced injury. *Respir Res* 13, 107 (2012).
15. E. G. O'Koren, B. L. Hogan, M. D. Gunn, Loss of basal cells precedes bronchiolitis obliterans-like pathological changes in a murine model of chlorine gas inhalation. *Am J Respir Cell Mol Biol* 49, 788-797 (2013).
16. M. Trevisani et al., 4-Hydroxynonenal, an endogenous aldehyde, causes pain and neurogenic inflammation through activation of the irritant receptor TRPA1. *Proc Natl Acad Sci USA* 104, 13519-13524 (2007).
17. B. F. Bessac et al., TRPA1 is a major oxidant sensor in murine airway sensory neurons. *J Clin Invest* 118, 1899-1910 (2008).
18. J. P. Henderson, J. Byun, J. W. Heinecke, Molecular chlorine generated by the myeloperoxidase-hydrogen peroxide-chloride system of phagocytes produces 5-chlorocytosine in bacterial RNA. *J Biol Chem* 274, 33440-33448 (1999).
19. T. K. McGovern et al., Neutrophils mediate airway hyperresponsiveness after chlorine-induced airway injury in the mouse. *Am J Respir Cell Mol Biol* 52, 513-522 (2015).
20. V. S. Bebarta et al., Hydroxocobalamin and sodium thiosulfate versus sodium nitrite and sodium thiosulfate in the treatment of acute cyanide toxicity in a swine (*Sus scrofa*) model. *Ann Emerg Med* 55, 345-351 (2010).
21. M. Brenner et al., Oral Glycine and Sodium Thiosulfate for Lethal Cyanide Ingestion. *J Clin Toxicol*7, (2017).
22. J. Honavar et al., Nitrite therapy improves survival postexposure to chlorine gas. *Am J Physiol Lung Cell Mol Physiol* 307, L888-894 (2014).
23. A. F. Holleman, E. Wiberg, *Inorganic Chemistry*. (Academic Press, San Diego, 2001).
24. Y. Hu, G. Xie, D. M. Stanbury, Oxidations at Sulfur Centers by Aqueous Hypochlorous Acid and Hypochlorite: Cl(+) Versus O Atom Transfer. *Inorg Chem* 56, 4047-4056 (2017).
25. J. S. Cicone, J. B. Petronis, C. D. Embert, D. A. Spector, Successful treatment of calciphylaxis with intravenous sodium thiosulfate. *Am J Kidney Dis* 43, 1104-1108 (2004).
26. S. Adirekkiat et al., Sodium thiosulfate delays the progression of coronary artery calcification in haemodialysis patients. *Nephrol Dial Transplant* 25, 1923-1929 (2010).
27. W. K. Jacyk, Four common infectious skin conditions Tinea corporis, *Pityriasis versicolor*, Scabies, Larva migrans. *SA Fam Pract* 46, 13-16 (2004).
28. J. A. Perez Fidalgo et al., Management of chemotherapy extravasation: ESMO-EONS Clinical Practice Guidelines. *Ann Oncol* 23 Suppl 7, vii167-173 (2012).
29. C. E. Pfeifle et al., High-dose cisplatin with sodium thiosulfate protection. *J Clin Oncol* 3, 237-244 (1985).
30. D. R. Freyer et al., Effects of sodium thiosulfate versus observation on development of cisplatin-induced hearing loss in children with cancer (ACCL0431): a multicentre, randomised, controlled, open-label, phase 3 trial. *Lancet Oncol* 18, 63-74 (2017).
31. E. A. Neuwelt et al., First evidence of otoprotection against carboplatin-induced hearing loss with a two-compartment system in patients with central nervous system malignancy using sodium thiosulfate. *J Pharmacol Exp Ther* 286, 77-84 (1998).
32. M. Sakaguchi et al., Sodium thiosulfate attenuates acute lung injury in mice. *Anesthesiology* 121, 1248-1257 (2014).
33. H. Yamamoto, Protection against paraquat-induced toxicity with sulfite or thiosulfate in mice. *Toxicology* 79, 37-43 (1993).
34. S. Ravindran, S. R. Boovarahan, K. Shanmugam, R. C. Vedarathinam, G. A. Kurian, Sodium Thiosulfate Preconditioning Ameliorates Ischemia/Reperfusion Injury in Rat Hearts Via Reduction of Oxidative Stress and Apoptosis. *Cardiovasc Drugs Ther* 31, 511-524 (2017).
35. S. Ravindran, S. Jahir Hussain, S. R. Boovarahan, G. A. Kurian, Sodium thiosulfate post-conditioning protects rat hearts against ischemia reperfusion injury via reduction of apoptosis and oxidative stress. *Chem Biol Interact* 274, 24-34 (2017).
36. U. Sen et al., Cardioprotective role of sodium thiosulfate on chronic heart failure by modulating endogenous H2S generation. *Pharmacology* 82, 201-213 (2008).
37. A. Pasch et al., Sodium thiosulfate prevents vascular calcifications in uremic rats. *Kidney Int*74, 1444-1453 (2008).
38. C. A. LaGrange, S. M. Lele, V. M. Pais, Jr., The effect of sodium thiosulfate administration on nephrocalcinosis in a rat model. *J Endourol* 23, 529-533 (2009).
39. P. M. Snijder et al., Sodium thiosulfate attenuates angiotensin II-induced hypertension, proteinuria and renal damage. *Nitric Oxide* 42, 87-98 (2014).
40. R. K. Bijarnia, M. Bachtler, P. G. Chandak, H. van Goor, A. Pasch, Sodium thiosulfate ameliorates oxidative stress and preserves renal function in hyperoxaluric rats. *PLoS One* 10, e0124881 (2015).
41. B. Myslovaty, S. Kyzer, H. Levinsky, C. Chaimoff, Improvement of rat survival and liver mitochondrial function in biliary obstruction after treatment with sodium thiosulfate. *HPB Surg* 8, 249-252 (1995).
42. E. Marutani et al., Thiosulfate Mediates Cytoprotective Effects of Hydrogen Sulfide Against Neuronal Ischemia. *J Am Heart Assoc* 4, (2015).
43. M. Lee, E. G. McGeer, P. L. McGeer, Sodium thiosulfate attenuates glial-mediated neuroinflammation in degenerative neurological diseases. *J Neuroinflammation* 13, 32 (2016).
44. L. L. Muldoon et al., Delayed administration of sodium thiosulfate in animal models reduces platinum ototoxicity without reduction of antitumor activity. *Clin Cancer Res* 6, 309-315 (2000).
45. X. Tian et al., Acute lung injury induced by chlorine inhalation in C57BL/6 and FVB/N mice. *Inhal Toxicol* 20, 783-793 (2008).
46. Y. Mo, J. Chen, C. F. Schlueter, G. W. Hoyle, Differential susceptibility of inbred mouse strains to chlorine-induced airway fibrosis. *Am J Physiol Lung Cell Mol Physiol* 304, L92-102 (2013).
47. G. W. Hoyle, W. Chang, J. Chen, C. F. Schlueter, R. J. Rando, Deviations from Haber's Law for multiple measures of acute lung injury in chlorine-exposed mice. *Toxicol Sci* 118, 696-703 (2010).
48. D. A. Ford et al., Formation of chlorinated lipids post-chlorine gas exposure. *J Lipid Res* 57, 1529-1540 (2016).
49. T. K. McGovern et al., Dimethylthiourea protects against chlorine induced changes in airway function in a murine model of irritant induced asthma. *Respir Res* 11, 138 (2010).
50. T. McGovern, B. J. Day, C. W. White, W. S. Powell, J. G. Martin, AEOL10150: a novel therapeutic for rescue treatment after toxic gas lung injury. *Free Radic Biol Med* 50, 602-608 (2011).
51. S. A. Tuck et al., Time course of airway remodelling after an acute chlorine gas exposure in mice. *Respir Res* 9, 61 (2008).
52. T. McGovern et al., CysLT1 Receptor Is Protective against Oxidative Stress in a Model of Irritant-Induced Asthma. *J Immunol* 197, 266-277 (2016).
53. Y. Hamamoto et al., Montelukast reduces inhaled chlorine triggered airway hyperresponsiveness and airway inflammation in the mouse. *Br J Pharmacol* 174, 3346-3358 (2017).
54. S. Ano et al., Inflammation and airway hyperresponsiveness after chlorine exposure are prolonged by Nrf2 deficiency in mice. *Free Radic Biol Med* 102, 1-15 (2017).
55. H. C. O'Neill et al., Treatment with the catalytic metalloporphyrin AEOL 10150 reduces inflammation and oxidative stress due to inhalation of the sulfur mustard analog 2-chloroethyl ethyl sulfide. *Free Radic Biol Med* 48, 1188-1196 (2010).
56. H. C. O'Neill et al., Role of reactive oxygen and nitrogen species in olfactory epithelial injury by the sulfur mustard analogue 2-chloroethyl ethyl sulfide. *Am J Respir Cell Mol Biol* 45, 323-331 (2011).
57. C. S. McElroy et al., From the Cover: Catalytic Antioxidant Rescue of Inhaled Sulfur Mustard Toxicity. *Toxicol Sci* 154, 341-353 (2016).

58. L. A. Veress et al., Tissue plasminogen activator prevents mortality from sulfur mustard analog-induced airway obstruction. *Am J Respir Cell Mol Biol* 48, 439-447 (2013).
59. J. D. Chandler et al., Antiinflammatory and Antimicrobial Effects of Thiocyanate in a Cystic Fibrosis Mouse Model. *Am J Respir Cell Mol Biol* 53, 193-205 (2015).
60. N. S. Gould, E. Min, R. J. Martin, B. J. Day, CFTR is the primary known apical glutathione transporter involved in cigarette smoke-induced adaptive responses in the lung. *Free Radic Biol Med* 52, 1201-1206 (2012).
61. S. O. Abarikwu, A. B. Pant, E. O. Farombi, 4-Hydroxynonenal induces mitochondrial-mediated apoptosis and oxidative stress in SH-SY5Y human neuronal cells. *Basic Clin Pharmacol Toxicol* 110, 441-448.
62. S. Farese et al., Sodium thiosulfate pharmacokinetics in hemodialysis patients and healthy volunteers. *Clin J Am Soc Nephrol* 6, 1447-1455 (2011).
63. M. Shea, J. A. Koziol, S. B. Howell, Kinetics of sodium thiosulfate, a cisplatin neutralizer. *Clin Pharmacol Ther* 35, 419-425 (1984).
64. L. P. Liang et al., Neuroprotective Effects of AEOL10150 in a Rat Organophosphate Model. *Toxicol Sci*, (2017).

What is claimed is:

1. A method of treating chlorine-gas induced lung injury in a subject comprising administering to the subject a therapeutically effective amount of sodium thiosulfate, wherein the subject is a human.

2. The method of claim 1, wherein the lung injury is selected from the group consisting of acute respiratory distress syndrome (ARDS), chronic obstructive pulmonary disease (COPD), chemical induced asthma, pulmonary fibrosis, interstitial lung disease, pulmonary edema, pneumonitis and cystic fibrosis lung disease.

3. The method of claim 1, wherein the sodium thiosulfate is administered to the subject by an administration route selected from the group consisting of ocular, oral, subcutaneous (SC), intramuscular (IM), and intravenous (IV).

4. The method of claim 1, wherein the sodium thiosulfate is administered to the airway of the subject by a delivery method selected from the group consisting of inhalation, nebulization, aerosolization and intratracheal delivery.

5. The method of claim 1, wherein the sodium thiosulfate is administered to the eye of the subject by an ocular delivery system.

6. The method of claim 5, wherein the ocular delivery system is eye drops.

7. The method of claim 1, wherein the step of administering comprises administering to the subject an initial dose of the sodium thiosulfate followed by administering an additional dose of the sodium thiosulfate to the subject.

8. The method of claim 1, wherein the step of administering the sodium thiosulfate is conducted following the exposure of the subject to chlorine gas.

9. The method of claim 1, wherein the step of administering the sodium thiosulfate is conducted immediately after an initial exposure of the subject to chlorine gas.

10. The method of claim 1, wherein the step of administering the sodium thiosulfate is conducted within about 1 hour to about 24 hours after an initial exposure of the subject to chlorine gas.

11. The method of claim 1, wherein the sodium thiosulfate is administered at least 1 hour to 2 weeks after exposure of the subject chlorine gas.

12. The method of claim 1, wherein the step of administering the sodium thiosulfate is commenced at the onset of acute lung injury symptoms in the subject.

13. The method of claim 1, wherein sodium thiosulfate is administered for at least one week.

* * * * *